[19] United States Patent
Kamatani et al.

[11] 4,011,135
[45] Mar. 8, 1977

[54] PRODUCTION OF L(+)-TARTARIC ACID

[75] Inventors: Yoshio Kamatani, Osaka; Hisayoshi Okazaki, Kyoto; Ko Imai, Osaka; Noriaki Fujita, Suita; Yoshio Yamazaki, Toyonaka; Katsuhiko Ogino, Osaka, all of Japan

[73] Assignee: Takeda Chemical Industries, Ltd., Japan

[22] Filed: Jan. 19, 1976

[21] Appl. No.: 650,025

[30] Foreign Application Priority Data

Jan. 17, 1975 Japan .............................. 50-8149

[52] U.S. Cl. ................................................. 195/30
[51] Int. Cl.$^2$ .......................................... C12D 1/02
[58] Field of Search ..................................... 195/30

[56] References Cited
OTHER PUBLICATIONS

Martin, et al., J. of Bacteriology, vol. 70, pp. 405–414 (1955).

Primary Examiner—Alvin E. Tanenholtz
Attorney, Agent, or Firm—Wenderoth, Lind & Ponack

[57] ABSTRACT

L(+)-tartaric acid is produced in a high efficiency from cis-epoxysuccinic acid by a microorganism belonging to the genus Pseudomonas, Agrobacterium or Rhizobium.

13 Claims, No Drawings

PRODUCTION OF L(+)-TARTARIC ACID

This invention relates to a new method for producing natural-type L(+)-tartaric acid from cis-epoxy succinic acid, by utilizing microorganisms.

L(+)-tartaric acid is in a great demand, being used as an acidulant in foods; and it has been conventional practice in the field of the art to obtain the tartaric acid as the by-product in the course of wine-brewing processes. Such by-product has its limit in supply, which is a drawback to the stabilized production of large amounts of L(+)-tartaric acid. For overcoming the deficiency, various methods for production have been contemplated or examined, such as the methods of chemical syntheses from fumaric acid, maleic acid, 5-ketogluconic acid, etc., or the methods of direct fermentation of tartaric acid through the utilization of microorganisms. However, all of those methods have untoward disadvantages such that the isomers of non-natural type come out vainly as by-products, or that merely deficient yields of tartaric acid are gained, which facts have totally defied their utilization for the industrialized production of tartaric acid.

Taking those predicaments in view, the present inventors have devoted deep studies to an entirely innovated method in which cis-epoxysuccinic acid which can be supplied in large amounts is utilized as the raw material, upon which the microorganisms are made to act, so that the stereo specific hydrolysis may effectively take place, thereby obtaining L(+)-tartaric acid alone in high yield; and thus the studies have finally led to the completion of this invention.

Thus, the first object of this invention is to provide a new microbial process for producing L(+)-tartaric acid.

The second object of this invention is to provide microorganisms which are capable of hydrolyzing cis-epoxysuccinic acid to L(+)-tartaric acid.

Further objects will be explained in the following descriptions.

The present method for producing L(+)-tartaric acid comprises; having the culture of microorganisms, or the processed matter thereof, which is capable of hydrolyzing cis-epoxysuccinic acid belonging to genus Pseudomonas, Agrobacterium, or Rhizobium, thereby producing L(+)-tartaric acid, brought in contact with cis-epoxy succinic acid, and recovering so-produced L(+)-tartaric acid.

The microorganisms to be employed in this invention can be isolated to remarkable advantage from among the microorganisms which are capable of growing in the culture medium containing cis-epoxy succinic acid as the sole carbon source. There may be exemplified such an isolation process in which, firstly, a culture medium (pH 7.0) is set up by adding 0.5—2 % of cis-epoxysuccinic acid, as the sole carbon source, to the basic culture medium which contains sodium nitrate (0.2 %), dipotassium phosphate (0.1 %), magnesium sulfate (0.05 %), potassium chloride (0.05 %) and ferrous sulfate (0.001 %); and secondly, a proper amount of sample such as soil, plant body, root nodule, or other like substance, is to be added to said culture medium; and thirdly, the above result is subjected to shaking culture for 3–5 days at a temperature range of 24° C–37° C; and finally, the isolation is carried out with respect to the microorganism that has grown up therein.

Among the microorganisms having been obtained as above, the microbial strains which the present inventors designated with such numbers as KB-86, -91, -97, -105 and -106, are utilized, granting that they serve the purpose of this invention.

The particulars of the bacteriological characteristics of these microbes are described below:

1. Taxonomic properties of the strain KB-86 a. Cell morphology.
 1. Rods, 0.6–0.8 by 1.5–3.0 μm.
 2. Not pleomorphic
 3. Motile by polar monotrichous flagellum
 4. Non-sporing
 5. Gram-negative
 6. Non-acid-fastness b. Cultural characteristics.
 1. Nutrient agar plate: Circular, entire, convex, translucent, creamy white, glistening
 2. Agar slant: Growth moderate, filiform, smooth, creamy white, glistening
 3. Broth: Slightly turbid; no surface growth; sediment
 4. Gelatin stab: No liquefaction
 5. Litmus milk: Unchanged c. Physiological properties:
 1. Nitrates are not reduced in nitrate broth.
 2. Denitrification does not occur.
 3. Methyl red test is negative.
 4. Acetylmethylcarbinol is not produced.
 5. Indole is not produced.
 6. Hydrogen sulfide is not produced.
 7. Starch is not hydrolized.
 8. Citrate is utilized.
 9. Nitrates and ammonium salts are utilized as nitrogen sources.
 10. Water soluble pigments are not produced.
 11. Urease is produced.
 12. Oxidase: positive.
 13. Catalase: positive.
 14. No growth at pH 6.0 and 10.5. Optimal pH, at about 7. No growth at 40° C. Growth at 10° C. Optimal temperature, between 25° C and 30° C.
 15. Aerobic.
 16. Hugh and Leifson test: oxidative.
 17. Acid but no gas from L-arabinose, D-xylose, D-glucose, D-mannose, D-fructose, D-galactose, maltose, sucrose, trehalose, D-sorbitol, D-mannitol, and glycerol. No acid and no gas from lactose, inositol, and starch.

d. Other taxonomic properties.
 1. Nitrogen fixation does not occur.
 2. Amino acids and vitamins are not necessary for growth.
 3. Isolated from soil.

2. Taxonomic properties of the strain KB-91.

a. Cell morphology.
 1. Rods, 0.5–0.7 by 1.0–3.0 μm.
 2. Not pleomorphic.
 3. Motile by one to three peritrichous flagella.
 4. Non-sporing.
 5. Gram-negative.
 6. Non-acid-fastness.

b. Cultural characteristics
 1. Nutrient agar plate: Circular, spreading, convex, transparent, yellow, glistening.
 2. Agar slant: Growth moderate, spreading, smooth, yellow, glistening.

3. Broth; Turbid; no surface growth; sediment.
4. Gelatin stab: Stratiform liquefaction.
5. Litmus milk: Neutral to slightly alkaline without serum zone. No peptonization. Grayish brown color after 2 weeks.

c. Physiological properties.
1. Nitrates are not reduced in nitrate broth.
2. Denitrification does not occur.
3. Methyl red test negative.
4. Acetylmethylcarbinol is not produced.
5. Indole is not produced.
6. Hydrogen sulfide is not produced.
7. Starch is not hydrolized.
8. Citrate is utilized.
9. Nitrates and ammonium salts are utilized as nitrogen sources.
10. Chromogenic.
11. Urease is produced.
12. Oxidase: positive.
13. Catalase: positive.
14. No growth at pH 4.5 and 10.5. Optimal pH, at about 7. No growth at 40° C. Growth at 10° C. Optimal temperature, at about 30° C.
15. Aerobic.
16. Hugh and Leifson test: oxidative.
17. Acid but no gas from L-arabinose, D-glucose, D-mannose, D-fructose, D-galactose, lactose, trehalose, D-sorbitol, D-mannitol, inositol. No acid and no gas from D-xylose, maltose, sucrose, glycerol, and starch.

d. Other taxonomic properties.
1. 3-Ketolactose production test: positive.
2. Amino acids and vitamins are not necessary for growth.
3. Growth on aniline blue glucose agar. Dye is not absorbed.
4. Cellulose is not decomposed.
5. Isolated from soil.
6. Not parasitic for plants as checked.

3. Taxonomic properties of the strain KB-105.

a. Cell morphology.
1. Rods, 0.5—0.7 by 1.0-3.0 $\mu$m.
2. Not pleomorphic.
3. Motile by one to three peritrichous flagella.
4. Non-sporing.
5. Gram-negative.
6. Non Acid fastness.

b. Cultural characteristics.
1. Nutrient agar plate: circular, entire, convex, smooth, opaque, yellowish white, glistening.
2. Agar slant: Growth moderate, filiform, yellowish white, glistening.
3. Broth: Sediment, pellicle.
4. Gelatin stab: No liquefaction.
5. Litmus milk: Alkaline with serum zone.

c. Physiological properties.
1. Nitrates are not reduced in nitrate broth.
2. Denitrification does not occur.
3. Methyl red test: negative.
4. Acetylmethylcarbinol is not produced.
5. Indole is not produced.
6. Hydrogen sulfide is not produced.
7. Starch is not hydrolized.
8. Citrate is utlized in Christensen's medium but not in Koser's medium.
9. Nitrates and ammonium salts are utilized as nitrogen sources.
10. Achromogenic.
11. urease is produced.
12. Oxidase: positive.
13. Catalase: positive.
14. No growth at pH 4.5 and 10.5. Optimal pH, at about 7. No growth at 40° C. Growth at 10° C. Optimal temperature, at about 30° C.
15. Aerobic.
16. Hugh and Leifson test: oxidative.
17. Acid but no gas from L-arabinose, D-xylose, D-gulcose, D-mannose, D-fructose, D-galactose, maltose, sucrose, trehalose, D-sorbitol, D-mannitol, and glycerol. No acid and no gas from lactose, inositol, and starch.

d. Other taxonomic properties.
1. 3-Ketolactose production test: positive.
2. Vitamin necessary for growth.
3. Growth on aniline blue glucose agar. Dye is not absorbed.
4. Viscous colonies are formed on sugar media.
5. Cellulose is not decomposed.
6. Isolated from sail.
7. Not parasitic for plants as checked.

4. Taxonomic properties of the strains KB-97 and KB-106.

a. Cell morphology.
1. Short rods, 0.8–1.0 by 1.0–1.5 $\mu$m.
2. In young cultures large irregular cells are found. In older cultures the cells become coccoid rods.
3. Non-motile.
4. Non-sporing.
5. Gram-negative.
6. Non-acid-fastness.

b. Cultural characteristics.
1. Nutrient agar plate: circular, entire, convex, smooth, grayish white, opaque, glistening.
2. Agar slant: Growth moderate, filiform, smooth, grayish white, glistening.
3. Broth: Slightly turbid; no surface growth; sediment.
4. Gelatin stab: No liquefaction.
5. Litmus milk: Slightly alkaline; not peptonized; no serum zone.

c. Physiological properties.
1. Nitrate reduction: KB-106 is positive but KB-97 is negative in nitrate broth.
2. Denitrification does not occur.
3. Methyl red test: negative.
4. Acetylmethylcarbinol is not produced.
5. Indole is not produced.
6. Hydrogen sulfide is not produced.
7. Starch is not hydrolized.
8. Citrate is not utilized.
9. Nitrates and ammonium salts are utilized as nitrogen sources.
10. Achromogenic.
11. Urease is produced.
12. Oxidase: positive.
13. Catalase: positive.
14. No growth at pH 4.5 and 8.6. Optimal pH, at about 7.
No growth at 40° C. Growth at 10° C. Optimal temperature, at about 30° C.
15. Aerobic.
16. Hugh and Leifson test: oxidative.
17. Acid but no gas from L-arabinose, and D-fructose. Slightly acid but no gas from D-xylose, D- glucose, D-mannose, D-galactose, and glycerol. No acid and no gas from maltose, sucrose, lactose, trehalose, D-sorbitol, D-mannitol, inositol, and starch.

d. other taxonomic properties.
 1. 3-Ketolactose is not produced.
 2. Growth on yeast extract media within 3 days.
 3. Isolated from root nodules of clover.

Taxonomic properties of these 5 strains were consulted with descriptions in Bergey's Manual of Determinative Bacteriology, 8th edition (1974), and taxonomic positions of these strains were identified.

The strain KB-86 is identified as a species of the genus Pseudomonas, because this organism is gram-negative, oxidase-positive, aerobic, motile rod, possesses polar monotrichous flagellum, and does not grow at pH 6.0.

The strains KB-91 and KB-105 are identified as the species of the genus Agrobacterium, because these two organisms are gram-negative, aerobic, oxidase-positive, catalase-positive, and motile rods, utilize citrate, and give positive reaction in 3-ketolactose production test. But these organisms are not found to be parasitic for plants as checked and do not reduce nitrates in nitrate broth. In addition the strain KB-91 is chromogenic, and the strain KB-105 requires vitamin for its growth, and both organisms are determined to be new species of the genus Agrobacterium. Thus, the strain KB-91 is named Agrobacterium aureum, and KB-105 is named Agrobacterium viscosum, respectively.

The strains KB-97 and KB-106 were isolated from root nodules of clover. These two organisms are gram-negative, aerobic rods, do not produce 3-ketolactose, and do not utilize citrate. Young cells are irregular and large, and in older cultures the cells become coccoid rods. From these properties, the strains KB-97 and KB-106 are identified as a species of the genus Rhizobium. But both organisms are non-motile, grow on yeast extract media within 3 days and cause litmus milk to alkaline without serum zone. Thus, the strains KB-97 and KB-106 are determined to be new species of the genus Rhizobium and they are both named Rhizobium validum.

The above designated microbes are currently deposited under the custody of:
"Institute for Fermentation", (A Judicial Foundation; abridged name: IFO): Osaka, Japan
"Fermentation Research Institute, Agency of Industrial Science & Technology" (abridged name: FERM), Chiba-City, Japan; and
"American Type Culture Collection (abridged name: ATCC)", Maryland, U.S.A.

And, the identifying numbers are assigned to each of the microorganisms as are listed below:

| Microorganism | IFO No. | FERM Accession No. | ATCC No. |
|---|---|---|---|
| KB-86 | 13645 | 2855 | 31106 |
| KB-91 | 13647 | 2857 | 31108 |
| KB-97 | 13648 | 2858 | 31109 |
| KB-105 | 13652 | 2862 | 31113 |
| KB-106 | 13653 | 2863 | 31114 |

The method which represents this invention is to be carried out by bringing the cultures of above-described microbes or the treated material thereof into contact with cis-epoxysuccinic acid which is the raw material to be employed. In the instance when the culture is to be brought to contact, as for this culture, there may be employed the product per se which has been obtained from the incubation of the intended microbe, in one way; while as an alternative means the cis-epoxysuccinic acid may be added to the culture medium, during the course of microbe-incubation process, thereby actuating a simultaneous parallel performance of both the microbe-incubation and the reaction.

The processed matter of the culture as herein mentioned represent the specimens that contain exzyme system which is related to the reaction in which cis-epoxysuccinic acid is hydrolyzed, resulting in the formation of L(+)-tartaric acid. To exemplify said samples, they are live microbial cells, dry microbial cells, entrapped microbial cells, ground microbial cells, raw or refined enzyme, insolubilized enzyme, or the like, which are obtained by having the said culture subjected to adequate treatments, e.g., centrifugal isolation, filtration, washing, drying, grinding, extraction, insolubilization, or like procedures.

Upon practicing the said incubation work, the culture medium may be either in liquid or solid state; but commonly applicable as well as more convenient way is to resort to the shaking culture or the aerated agitation culture to be done as based on the liquid-state culture medium. There is not any particular limitation or condition in determining the sort of the culture medium, that is, any sort of culture medium may be employed to the extent that the culture medium can accommodate said microbes allowing them to grow up normally, and that the enzyme system capable of converting the cis-epoxy succinic acid into L(+)-tartaric acid can be properly formed therein. For example, as the carbon source to be employed, the cis-epoxysuccinic acid, glucose, lactose, glycerin, sucrose, molasses, organic acids, hydrocarbons, and the like, may be used; and as the nitrogen source, various classes of ammonium salt, nitrate, or other nitrogen compounds may be used; and further, as for the inorganic salts, various classes of phosphate, magnesium sulfate, sodium chloride, etc. may be added. Also, for the purpose of encouraging the growth of microorganisms, various vitamins, compounds associated with nucleic acid or the like, may be added. Whatever incubating method may be adopted in the actual working instance, it is advisable to add, at the starting time of incubation, the cis-epoxysuccinic acid into the culture medium, even if in small amount, in that it is efficacious to bring about a better result.

Moreover, depending upon the kind of culturing method and upon conditions of incubation, the adding of some defoaming agent, such as silicone, soybean oil or the like, to the culture medium may in some cases turn out to be effective for enhancing the yield rate of L(+)-tartaric acid production. Again, when setting out on the incubation work, it is preferable to inoculate into the culture medium some proper amount of culture broth obtained through the pre-culturing which has been done beforehand in a minor scale. The incubating conditions, involving culturing temperature, duration of culturing time, and acidity-alkalinity of the culture medium, are subject to variation according to the kind of microbes employed or to the composition or elements of the culture medium; but, if only adequate selection and adjustment are done simply aiming at the ultimate target of maximum production of said enzyme system, it would justify the working conditions, sufficing the objective. In many cases of practice, good results can be obtained by making incubation under aerobic conditions, at around 20°–40° C, and for 1–7 days, meanwhile maintaining the culture broth at around pH 5–9.

On the occasion when the raw material cis-epoxysuccinic acid is to be added to the culture medium in the course of incubating process, as for the timing of the addition of material, the choice generally falls on either prior to the starting time of incubation, or on the adequate time during the incubating progress. In this instance, said material to be added is to be arranged into powdery form of, for example, sodium, potassium, or other like salts, or else, into the form of solution or suspension which is melted or dissolved in proper solvent such as water; and said solution or suspension is to be added all at one time, or continuously ranging over a definite period of time, or intermittently.

In the case where it is intended to produce L(+)-tartaric acid by the method of bringing the raw materials into contact with the culture of the microorganism, or with the treated substance thereof, ordinarily it is preferable to make said inoculation in an aqueous medium. In this instance, more advantageous result may be obtained by making the concentration of cis-epoxysuccinic acid in the reactant liquid as higher as possible, provided that said concentration be kept within the bounds not to impede the activity of the microbial culture or the processed matter thereof. If circumstances so require, it is feasible that the cis-epoxysuccinic acid be added in parts, at intervals of a certain definite period of time.

Reaction may be initiated by whichever one of the methods of standing, shaking or agitating. Further in the case where the entrapped microbial cells or the insolubilized enzyme is utilized, such a method is also applicable that the cis-epoxysuccinic acid solution is let flow through the column in which said utilized substance is filled up. As for the reaction temperature, in ordinary cases around 5°–50° C is used. The velocity of reaction varies according to such variable factors as the kind of microbes used, the amount of enzyme which is contained in the culture or its processed matter, the concentration of cis-epoxysuccinic acid, the mode of reaction as well as the reaction conditions; and therefore, the reaction time is to be determined by the adequate selection as the circumstances demand.

L(+)-tartaric acid having been formed in the culture broth or in the reaction medium through the mechanisms as have been described above can be easily isolated by a proper combination of various methods, as being based on the specific chemical characteristics of L(+)-tartaric acid. By way of examples, the precipitation as calcium salts or the like, or the impurities elimination method by means of ion exchange resin, activated charcoal and the like is used, each of which gaining effective results.

While the preferred embodiments of the methods pertaining to this invention are shown in the following examples, it is to be understood that the following examples are described for illustrating purposes only, and it will be obvious that the methods disclosed in detail are not to be construed as limitations of the contents of this invention.

EXAMPLE 1

A strain of *Rhizobium validum* KB-97 is used to inoculate 500 ml of liquid culture medium (pH 7.0) contained in two sets of 2 l-capacity Sakaguchi flasks, the medium being composed of glucose (0.5 %), ammonium nitrate (0.5 %), dipotassium phosphate (0.1 %), plus magnesium sulfate (0.05%); and this liquid culture medium is subjected to incubation under reciprocating-shaking culture at 30° C for 24 hours, obtaining therefrom around 1 l of culture broth. The broth thus obtained is transferred into a tank of 50 l-capacity which contains 30 l of liquid culture medium (pH 7.0) being composed of disodium cisepoxysuccinate (0.6%), ammonium nitrate, (0.5%), dipotassium phosphate (0.1 %), and magnesium sulfate (0.05 %); and the tank content is subjected to aerated agitation culture at 30° C for 30 hours. The culture broth obtained from the above (15 l) is transfused into a 200 l-capacity tank which contains 100 l of culture medium (pH 7.0) which is composed of ammonium nitrate (0.5 %), dipotassium phosphate (0.1 %), potassium chloride (0.05 %), magnesium sulfate (0.05 %), and ferrous sulfate (0.001 %); and simultaneously, 2.7 kg. of the crystals of disodium cis-epoxysuccinate is added. The mixture is subjected to aerated agitation culturing at 30° C. This culturing is done continuously for 7 running days; and along the going duration, each 2.0kg. of the crystals of disodium cis-epoxysuccinate is added on the 3rd day and on the 5th day, respectively. Around 95 l of the culture broth obtained as above is filtered by means of filterpress; and while agitating the filtrate thoroughly well, 5.8 kg of the crystals of calcium chloride (dihydrate) is added by piecemeal; and the result of the above is left standing for one night, following which filtration by means of filterpress is carried out; and thus the crystals of calcium L(+)-tartarate is recovered. Amount of yield comes up to 5.7 kg (as anhydride).

EXAMPLE 2

A strain of *Agrobacterium aureum* KB-91 is used to inoculate flasks, 500 ml each of liquid culture media (pH 7.0), respectively placed in four 2 l-capacity Sakaguchi flasks, each medium being composed of disodium cis-epoxysuccinate (0.6 %), ammonium nitrate (0.5 %), dipotassium phosphate (0.1 %), potassium chloride (0.05 %), magnesium sulfate (0.05 %), and ferrous sulfate (0.001 %); and this liquid culture medium is subjected to incubation under reciprocating-shaking culturing, at 28° C for 48 hours. Around 1.9 l of the culture broth obtained from the above is placed under centrifugal separation, thereby having the microbial cells collected, and thus around 5 g of wet cells. The wet cells are then suspended in 200 ml of distilled water, to which 5.2 g of the crystals of disodium cis-epoxysuccinate are added. The mixture is then driven toward reaction at 37° C, for 4 hours, shaking or stirring being given once and again at intervals. The reactant liquid obtained therefrom is subjected to centrifugal separation to eliminate the cells; and to the supernatant liquid of the above, 4.5 g of calcium chloride (dihydrate) is added by piecemeal, stirring being exerted all the while. After having been left standing in the refrigerator for one night, the precipitates formed therein are collected on the glass filter, which precipitates are then thoroughly rinsed with water; and thus, 5.1 g of the crystals (as anhydride) of calcium L(+)-tartarate are obtained.

EXAMPLE 3

A strain of *Agrobacterium viscosum* KB-105 is used to inoculate in the same manner as in Example 2 except for the addition of 100 μg/ml of pyridoxal, thus obtaining 6.0 g of wet cells. The cells are suspended in 50 ml of distilled water, and the suspension is caused to undergo ultrasonic wave treatment (140 W; 1.7 A) for 15 minutes. An amount of the treated liquid obtained through ultrasonic wave function is subjected to centrifugal separation (20,000 xg) for 15 minutes, thereby obtaining 47 ml of supernatant liquid. To this supernatant liquid, 50 ml of a 4.0 % aqueous solution of disodium cis-epoxysuccinate is added, and the mixture is rendered to reaction at 37° C for 2 hours. After termination of reaction, the reactant liquid is diluted twofold with water, which is then allowed to run through the activated charcoal column (1.5 × 10 cm), thereby collecting the eluate. While the agitation is being exerted, 15 ml of 12 % solution of calcium chloride is added dropwise. The result of the above is left standing at 5° C for 3 hours, and during which the precipitates are collected on the glass filter. Thus the crystals of calcium L(+)-tartarate are recovered, the yield coming up to 2.0 g (as anhydride).

EXAMPLE 4

A strain of *Pseudomonas sp.* KB-86 is used to inoculate and incubated in the same manner as in Example 2; and out of 4 l of the culture broth, around 11 g of wet cells is recovered. Thus recovered cells are suspended in 200 ml of distilled water, and to which 100 ml of aqueous solution which contains acrylamide (30 g), N,N'-methylene-bis-acrylamide (0.8 g), N,N,N',N'-tetramethyl-ethylene-diamine (0.2 ml), along with 100 ml of a 0.3 % aqueous solution of ammonium persulfate, are added. The resultant liquid is rendered to reaction at 0°–5° C for around 1 hour, so that gel may be formed up. The gel thus formed is then triturated substantially by means of homogenizer, then followed by the rinsing with 2 l of distilled water. The rinsed gel is next suspended in 900 ml of distilled water. To this resultant suspension liquid of entrapped cells, 100 ml of a 30 % solution of disodium cis-epoxysuccinate is added; and while the milder agitation is being exerted, the suspension liquid is rendered to reaction at 30° C for 10 hours. The reactant liquid is filtered through a column in which a small piece of absorbent cotton or wadding is packed up; and immediately following the above, 2 l of distilled water is let flow through the column, in order to effectuate the rinsing of the gel. The reactant-filtrate obtained from the above is made to join with the rinsing liquid, this blend then being subjected to desalting to be worked upon when passing through Amberlite IR-120 (H+ type) resin; and the eluate is subjected to concentration under reduced pressure. The resultant concentrate is left standing at 5° C for one night. The crystals formed therein during the night are collected on the glass filter, whereas the mother liquid is further concentrated. Through the repetition of concentration and crystallization, around 23 g of the crystals of L(+)-tartaric acid is recovered.

EXAMPLE 5

A strain of *Rhizobium validum* KB-106 is used to inoculate 500 ml of liquid culture medium (pH 7.0) contained in 2 l-capacity Sakaguchi flask, which is composed of disodium cis-epoxysuccinate (0.6 %), ammonium sulfate (0.5 %), dipotassium sulfate (0.1 %), plus magnesium sulfate (0.05 %); and this liquid culture medium is incubated at 30° C for 48 hours, under reciprocating-shaking culture, from which 500 ml of culture broth is obtained. The culture broth thus obtained is transferred to a tank of 50 l-capacity which contains 30 l of the culture medium just self-same in composition as the one described above; and the liquid culture medium in the said tank is subjected to incubation at 28° C for 48 hours under aerated, agitation culturing. Around 30 l of the culture broth obtained therefrom is placed under the action of Sharples Centrifuge for separating the microbial cells, and by which around 80 g of wet cells are obtained. These wet cells are suspended in 1.5 l of water, and by using Sorval Rf-1 Ribi Refrigerated Cell Fractionator the cells are completely destructed. After that, further centrifugal separation (20,000 xg) is exerted for 20 minutes, thus enabling to obtain around 1.4 l of supernatant liquid. Besides the above, another specific substance is employed herewith, i.e. $\beta$-1, 3-glucane (manufactured by TAKEDA Chemical Industries, Ltd. Japanese Patent is granted and registered with this substance, and is published under the serial number 32673/1973). This specific substance is produced by TAKEDA based on the strain NTK-u (IFO 13140) which is a mutant strain pertaining to genus *Alkaligenes faecalis* var mixogenes 10 C 3 K (This substance is hereinafter called PS for abbreviation). 300 g of PS is suspended in 6 l of distilled water, and to which 6 l of 5 % Bromocyanate aqueous solution is added; and while agitation is being exerted, 2N sodium hydroxide is applied dropwise at such a speed that pH will be raised by around 0.5 per minute; and the above is rendered to reaction so as to realize pH 11. Further, the reactant liquid is held standing at the above said pH value for 15 minutes. The reactant liquid is then filtered; and the solid part is thoroughly rinsed with distilled water; and as the result, an activated PS is obtained. To this activated PS obtained as above described, 1.4 l of previously obtained cell-extract, together with 3 l of 0.2M tris hydrochloric acid buffer solution (pH 8.0), are added. Distilled water is further added in order to allow the total volume to become 6 l., which is then made to proceed reaction at 5° C for 4 hours. After the termination of reaction, glass filter is used for filtration, thereby collecting the solid parts. Thence, in such order of 0.2M glycine, 0.5M sodium chloride and distilled water, rinsing is done for the amount of 8 l each, with the above respective ingredients. The insolubilized enzyme obtained therefrom is suspended in distilled water, and then filled up in the column (8 × 50 cm). While maintaining the above column at 30° C, 1.5 % aqueous solution of disodium cis-epoxysuccinate, which has been preheated up to 30° C in advance, is flown at a speed of 1.5 l per hour. To 72 l of column eluate which has been accumulated during 2 days past, 900 g of calcium chloride (dihydrate) is added by piecemeal, with agitation being exerted all the while. The resultant is left standing at room temperature for one night. The precipitates formed up therein is filtered and deciccated; and through which 1100 g of calcium L(+)-tartarate is recovered (as anhydride).

EXAMPLE 6

A strain of *Rhizobium validum* KB-97 is used to inoculate 500 ml of a liquid culture medium (pH 7.0) contained in 2 l-capacity Sakaguchi flask, which is composed of corn steep liquor (2.0 %), glucose (0.5 %) and this liquid culture is incubated at 28° C, for 24 hours, under reciprocating-shaking culture. Thus obtained culture broth is transferred to a tank of 50 l-capacity which contains 30 l of the culture medium just self-same in composition as the one described above and the liquid culture medium in the said tank is subjected to incubation at 28° C for 24 hours under aerated agitation culturing. Around 15 l of the culture broth obtained therefrom is transferred into a tank of 200 l-capacity which contains 100 l of a liquid culture medium composed of corn steep liquor (0.5 %), ammonium nitrate (0.1 %), sodium dihydrogen phosphate (0.2 %), magnesium sulfate (0.05 %), ferrous sulfate (0.001 %), polyoxyethylene lanolin derivative (0.1 %) (pH 7.0) and simultaneously 40 kg of calcium cis-epoxysuccinate (as free acid) is added.

The whole is subjected to aerated agitation culturing at 30° C for 30 hours. The resultant cultured broth and the washing water of the tank, about 150 l. in total are subjected to Decantor type centrifuge (Sumitomo Heavy Industries, Ltd. TS-210F type) to separate calcium L(+)-tartarate as crystals. The crystals are suspended in about 100 l. of water. After sufficiently stirring, the crystals are separated by said decantor type centrifuge and again suspended in about 70 l. of water and stirred well. The suspension is subjected to a filter-press to give 54 kg of calcium L(+)-tartarate (purity 98%) as anhydride.

What we claim is:

1. A method for producing L(+)-tartaric acid or salts thereof by hydrolysis of cis-epoxysuccinic acid which comprises (1) bringing a culture or processed matter containing an enzyme system thereof, obtained from a microorganism which belongs to the genus Pseudomonas, Agrobacterium or Rhizobium and said culture or enzyme system being capable of hydrolyzing cis-epoxysuccinic acid or salts thereof, thereby forming L(+)-tartaric acid, into contact with cis-epoxysuccinic acid or salts thereof in an aqueous medium at 5° to 50° C for a time sufficient to produce L(+)-tartaric acid and (2) recovering the so-formed L(+)-tartaric acid.

2. A method according to claim 1, wherein the microorganism is *Rhizobium validum*.

3. A method according to claim 1, wherein the microorganism is *Agrobacterium aureum*.

4. A method according to claim 1, wherein the microorganism is *Pseudomonas* species IFO 13645.

5. A method according to claim 1 wherein said processed matter contains live microbial cells.

6. A method according to claim 1 wherein said processed matter contains dry microbial cells.

7. A method according to claim 1 wherein said processed matter contains entrapped microbial cells.

8. A method according to claim 1 wherein said processed matter contains ground microbial cells.

9. A method according to claim 1 wherein said processed matter contains raw or refined enzyme.

10. A method according to claim 1 wherein said processed matter contains insolubilized enzyme.

11. A method according to claim 1 wherein the microorganism is *Agrobacterium aureum*, IFO 13647.

12. A method according to claim 1 wherein the microorganism is *Agrobacterium viscosum*, IFO 13652.

13. A method according to claim 1 wherein the microorganism is *Rhizobium validum*, IFP 13648 or 13653.

* * * * *